US006780848B2

(12) United States Patent
Gluckman et al.

(10) Patent No.: US 6,780,848 B2
(45) Date of Patent: Aug. 24, 2004

(54) USE OF GPE TO PROTECT GLIAL CELLS OR NON-DOPAMINERGIC CELLS FROM DEATH FROM NEURAL INJURY OR DISEASE

(75) Inventors: Peter D. Gluckman, Auckland (NZ); Christopher E. Williams, Auckland (NZ)

(73) Assignee: NeuronZ, Ltd., Auckland (NZ)

( * ) Notice: Subject to any disclaimer, the term of this patent is extended or adjusted under 35 U.S.C. 154(b) by 21 days.

(21) Appl. No.: 09/910,461

(22) Filed: Jul. 20, 2001

(65) Prior Publication Data

US 2002/0013277 A1 Jan. 31, 2002

Related U.S. Application Data

(63) Continuation of application No. 08/907,918, filed on Aug. 11, 1997, now abandoned, which is a continuation of application No. 08/656,331, filed as application No. PCT/NZ94/00143 on Dec. 20, 1994, now abandoned.

(30) Foreign Application Priority Data

| Dec. 23, 1993 | (NZ) | ............................................... 250572 |
| Mar. 14, 1994 | (NZ) | ............................................... 260091 |
| Jul. 22, 1994 | (NZ) | ............................................... 264070 |

(51) Int. Cl.$^7$ ........................... A61K 37/02; C07K 5/00

(52) U.S. Cl. ...................................... 514/18; 530/331

(58) Field of Search ...................... 514/18, 19; 530/331

(56) References Cited

U.S. PATENT DOCUMENTS

| 4,906,614 A | | 3/1990 | Giertz et al. ................... 514/18 |
| 5,032,109 A | * | 7/1991 | Sibalis .......................... 604/20 |
| 5,804,550 A | | 9/1998 | Bourguignon .................. 514/3 |

FOREIGN PATENT DOCUMENTS

| AU | A-52601/86 | 7/1986 |
| EP | 0 366 638 | 10/1989 |
| WO | WO 93/02695 | 2/1993 |
| WO | WO 93/21216 | 10/1993 |
| WO | WO 95/17204 | 6/1995 |
| WO | WO 95/17204 | 7/1995 |
| WO | WO 98/14202 | 4/1998 |
| WO | WO 99/65509 | 12/1999 |

OTHER PUBLICATIONS

Sara et al., Neurpactive Products of IGF–1 and IGF–2 Gene Expression in the CNS, *Molecular Biology and Physiology of Insulin–like Growth Factors*, pp. 439–448, edited by Raizade, M.K., and LeRoith, D., Plenum Press, N.Y. 1991.
Guan et al., The effects of IGF–1 treatment after hypoxic–ischemic brain injury in adult rats, Journal of Cerebral Blood Flow and Metabolism 13:609–616 (1993).
Sara, V. R., et al.: "The Biological Role of Truncated Insulin–Like Growth Factor–1 and The Tripeptide GPE In The Central Nervous System", Annals of the New York Academy of Sciences, vol. 692, pp. 183–191, (1991).
V. Sara et al, "*Identification of GLY–PRO–GLU (GPE), The Aminoterminal Tripeptide Of Insulin–Like Growth Factor 1 Which is Truncated In Brain, As A Novel Neuroactive Peptide*", Biochemical & Biophysical Research Communications vol. 165, No. 2, 1989, Dec. 15, 1989 pp 766–771.
L. Nilsson–Hakansson, et al., "*Effects of IGF–1, Truncated IGF–1 And The Tripeptide Gly–Pro–Glu On Acetylcholine Release From Parietal Cortex Of Rat Brain*", Neuroreport, 4,1111–1114(1993).
J. Saura, "*Neuroprotective Effects Of Gly–Pro–Glu, the N–terminal Tripeptide Of IGF–1, In The Hippocampus In Vitro*", Neuroreport vol. 10, pp. 161–164 (1999).
V. Sara, "*The Biological Role of Truncated Insulin–Like Growth Factor–1 and The Tripeptide GPE In The Central Nervous System*", Annals of the New York Academy of Sciences vol. 692, pp 183–191 (1998).

* cited by examiner

*Primary Examiner*—Bennett Celsa
(74) *Attorney, Agent, or Firm*—Fliesler Meyer LLP

(57) ABSTRACT

The tripeptide glycine-proline-glutamine (GPE) may be administered before, or usually after, injury to reduce damage to the central nervous system. GPE appears useful for neuronal rescue particularly but not exclusively within the hippocampus. Advantages of GPE include: (a) that it crosses the blood-brain barrier, so is effective by injected peripheral administration, (b) it is unlikely to challenge the immune system, (c) it is cheap, and (d) its therapeutic ratio is high. GPE may also be infused into the CSF. It may be administered prior to parturition or elective brain or cardiac surgery. Transdermal routes may be useful for chronic neural disorders. The CNS of mammals (including foetal mammals) after trauma including hypoxic/ischaemic experimental insults showed reduced damage under GPE protection as measured by histological assessment of cell damage or death and regional shrinkage.

37 Claims, 2 Drawing Sheets

USE OF GPE TO PROTECT GLIAL CELLS OR NON-DOPAMINERGIC CELLS FROM DEATH FROM NEURAL INJURY OR DISEASE

This application is a continuation of Application Ser. No. 08/907,918, filed Aug. 11, 1997 now abandoned. Application Ser. No. 08/907,918 is a continuation of abandoned Application Ser. No. 08/656,331, filed Jun. 14, 1996, Application Ser. No. 08/656,331 is a 371 of PCT International Application No. PCT/NZ94/00143, filed Dec. 20, 1994. PCT International Application No. PCT/NZ94/00143 claims the priority under 35 USC 119 of New Zealand Applications Nos. 250,572, filed Dec. 23, 1993; 260091, filed Mar. 14, 1994; and 264,070, filed Jul. 22, 1994.

TECHNICAL FIELD OF THE INVENTION

This invention relates to methods and therapeutic compositions for the treatment or prevention of central nervous system (CNS) cell damage in mammals—also peripheral nervous system protection—and more particularly relates to a method of increasing the concentration of specified naturally occurring or introduced 2- or 3-peptides within the central nervous system to treat an injury or disease affecting or liable to affect cells of the CNS (or PNS).

BACKGROUND OF THE INVENTION

The central nervous system is peculiar among mammalian organs in that differentiated neurones are practically incapable of regeneration. Permanent loss of function is a likely outcome of a sufficiently severe injury to the brain. It is particularly sad to meet children whose brains have been damaged by hypoxia during a difficult birth. There is therefore a need for means to protect cells of the central nervous system (also including the glial cells) from death after an injury.

After asphyxial, traumatic, toxic, infectious, degenerative, metabolic, ischaemic or hypoxic insults to the central nervous system (CNS) of man or other mammals a certain degree of damage in several different cell types may result. For example periventricular leucomalacia, a lesion which affects the periventricular oligodendrocytes is generally considered to be a consequence of hypoxic ischemic injury to the developing preterm brain (Bejar et al., Am. J. Obstet. Gynecol., 159:357–363 (1988); Sinha et al., Arch. Dis. Child., 65:1017–1020 (1990); Young et al., Ann. Neurol., 12:445–448 (1982)). Damage to the CNS by trauma, asphyxia, ischemia, toxins or infection is frequent and may cause sensory, motor or cognitive deficits. Glial cells which are non-neuronal cells in the CNS are necessary for normal CNS function. Infarcts are a principal component of some hypoxic ischemic induced damage and loss of glial cells is an essential component of infarction. There appears to be a kind of "delayed injury process" in which apparently "self-destructive" neural activity occurs some time after an injury; attempts to control this activity appear able to alleviate the effects of this delayed injury process.

Diseases of the CNS also may cause loss of specific populations of cells. For example multiple sclerosis is associated with loss of myelin and oligodendrocytes, similarly Parkinson's disease is associated with loss of dopaminergic neurons. Some situations in which CNS injury or disease can lead to predominant loss of neurons and/or other cell types include: perinatal asphyxia associated with fetal distress such as following abruption, cord occlusion or associated with intrauterine growth retardation; perinatal asphyxia associated with failure of adequate resuscitation or respiration; severe CNS insults associated with near-miss drowning, near-miss cot death, carbon monoxide inhalation, ammonia or other gaseous intoxication, cardiac arrest, collapse, coma, meningitis, hypoglycaemia and status epilepticus; episodes of cerebral asphyxia associated with coronary bypass surgery; cerebral anoxia or ischemia associated with stroke, hypotensive episodes and hypertensive crises; and cerebral trauma.

There are many other instances in which CNS injury or disease can cause damage to cells of the CNS. It is desirable to treat the injury in these instances. Also, it is desirable to prevent or reduce the amount of CNS damage which may be suffered as a result of induced cerebral asphyxia in situations such as cardiac bypass surgery.

We have previously shown (in New Zealand Patent Application No. 239211- "IGF-1 to improve neural outcome", the contents of which are hereby incorporated by way of reference) that the growth factor called insulin-like growth factor 1 (IGF-1) has an unanticipated action, namely to prevent brain cells from dying after an asphyxial or ischemic brain insult (Gluckman et al Biochem Biophys Res Commun 182:593–599 1992). Because insulin also has a neuroprotective action (Voll et al Neurology 41:423–428 (1991)) and insulin and IGF-1 can both bind to the IGF-1 receptor, it was generally assumed that this brain rescue mode of action of IGF-1 was mediated via the IGF-1 receptor (Guan et al J. Cereb. Blood Flow Metab. 13:609–616 (1993)).

It is known that IGF-1 can be modified by proteolytic cleavage in nervous tissue to des 1-3N IGF-1, that is IGF-1 missing the 3 amino acids from the amino terminal of the molecule, and hence after cleavage there is also a 3 amino acid peptide gly-pro-glu which is the N terminal tripeptide. This tripeptide is also termed GPE. As des 1-3N IGF-1 also binds to the IGF-1 receptor and GPE does not, the GPE was thought to be of no significance to the neuronal rescue action of IGF-1.

Our previous work had shown that the brain increases its production of IGF-1 following brain injury by hypoxia-ischemia and that in addition it increases the synthesis of two specific binding proteins, IGF binding protein-2 (IGFBP-2) and IGF binding protein-3 (IGFBP-3) (Gluckman et al Biochem Biophys Res Commun 182:593–599 1992) and Klemp et al Brain Res 18:55–61 (1992). These were hypothesised to attract the IGF-1 into the region of injury to reach concentrations necessary for neuronal rescue. For this reason IGF-1 was anticipated to be more potent given at a site distant from the injury than des 1-3 N IGF-1 which does not bind well to the binding proteins. This was indeed the case—des 1-3 N IGF-1 was not significantly active as a neuronal rescue agent at a dose equivalent to that at which IGF-1 shows neuronal rescue activity. Thus the prior art pointed to activity at the IGF-1 receptor as the mode of neuronal rescue achieved with IGF-1.

To date, there has been no enabling reference in the prior art to the manipulation of the cleaved tripeptide GPE itself to prevent or treat CNS injury or disease leading to CNS damage in vivo.

OBJECT OF THE INVENTION

It is an object of the invention to provide a method and/or medicament (therapeutic composition) for treating or preventing CNS damage which will go at least some way to meeting the foregoing desiderata in a simple yet effective manner or which will at least provide the public with a useful choice.

STATEMENT OF THE INVENTION

Accordingly, in a broad aspect the invention comprises a method of treating neural damage suffered by mammals (or patients) including the step of increasing the active concentration of the tripeptide GPE (the 3 amino acid peptide gly-pro-glu) and/or the concentration of analogues of GPE in the CNS of the mammal. In particular, the concentration of GPE in the CNS of the mammal is effectively increased.

Among preferred analogues of GPE are peptides selected from the group; gly pro glu (GPE), gly pro, and pro glu.

In a related aspect the invention relates to treatment for injury to the central nervous system (CNS) which is taken for the purpose of possible loci of activity of GPE to include those parts of the nervous system where cell bodies (including neurones and supporting cells such as glia, Schwann cells or the like) are located. Thus treatment of the peripheral nerves is a part of the invention as well as treatment of the brain, spinal cord, and the like.

More particularly the invention comprises a method for treating neuronal injury within at least the hippocampus.

(The term "treat" when used herein refers to at least attempting to effect a reduction in the severity of the CNS damage, by reducing neuronal loss, and loss of glial cells and other cells, suffered after a CNS injury. It encompasses the minimising of such damage following a CNS injury.)

(The term "injury" when used herein encompasses asphyxia, ischemia, stroke, toxins, infections, trauma, haemorrhage, and surgical damage to the CNS.)

Preferably, GPE and/or analogues thereof are administered to the patient directly. Alternatively, a compound may be administered which upon administration to the patient increases the active concentration of GPE or naturally occurring analogues of GPE in the CNS of the patient. For example, increasing the availability of IGF-1 may lead to increased concentrations of GPE.

Preferably, the medicament is administered in the period from before the time of injury and/or up to 100 hours after the CNS injury and more preferably 0.5 to 8 hours after the CNS injury.

Alternatively if an elective procedure is considered likely to lead to an injury to the CNS the medicament may be administered prior to the elective procedure, thereby arranging for raised levels of GPE during the procedure.

In a first form, preferably, said GPE and/or an analogue or analogues thereof selected from the group; gly pro glu, gly pro, pro glu, is administered by lateral cerebro-ventricular injection or through a surgically inserted shunt into the lateral cerebro ventricle of the brain of a patient in the inclusive period from the time of the CNS injury to 8 hours thereafter.

In another preferred form, GPE and/or an analogue or analogues thereof selected from the group; gly pro glu, gly pro, pro glu, is administered by injection into the cerebral parenchyma of a patient in the inclusive period from the time of the CNS injury to 8 hours thereafter.

In another preferred form of the present invention, GPE and/or an analogue or analogues thereof selected from the group; gly pro glu, gly pro, pro glu, is administered peripherally into a patient for passage into the lateral ventricle of the brain in the inclusive period of from the time of the CNS injury to 8 hours thereafter. By peripheral route, we mean an intravenous, oral, rectal, nasal, subcutaneous, inhalation, intraperitoneal or intramuscular route. Preferably, it is GPE itself that is administered by way of lateral cerebro ventricle injection or by use of the surgically inserted shunt.

Preferably the medicament is administered according to the pattern of injury or time lapsed after a CNS injury.

Preferably the dosage range administered is from about 0.1 μg to about 10 mg of GPE (or said analogue or said compound that elevates the concentration thereof) per 100 gm of body weight.

More preferably the dosage range administered is about 1 mg of GPE per 100 gm of body weight.

Optionally the dose rate may be about 10 μg/kg for infusion, in artificial CSF, into the lateral ventricle or other perfusion sites suitable for access to the CSF.

GPE (or said analogue or said compound that elevates the concentration thereof) may be used alone or in conjunction with other medicaments or growth factors designed to ameliorate against loss of CNS cells such as glia and neurons.

By "prevent" is meant a reduction in the severity of CNS damage suffered after a CNS injury and may consequently include inhibition of the symptoms of CNS damage.

In yet a further aspect, the invention provides the use of GPE and/or analogues thereof in the preparation of a medicament for treating CNS damage.

Alternatively, the invention comprises the use of a compound which, upon administration to a patient, increases the active concentration of GPE and/or naturally occurring analogues thereof in the CNS of the patient in the preparation of a medicament for treating injury to the CNS.

The invention also consists in a medicament suitable for treating CNS damage suffered after a CNS injury comprising GPE, and/or analogues thereof optionally provided in human dosage form in a pharmaceutically acceptable carrier or diluent.

In a related aspect the medicament comprising GPE may be provided together with suitable pharmaceutically acceptable excipients.

In a further related aspect the medicament comprising GPE may be provided in a manunalian dosage form.

In another related aspect the medicament for treating CNS damage may also comprise a compound or composition in human dosage form which, upon administration to the patient suffering CNS damage, increases the active concentration of GPE and/or naturally occurring analogues thereof in the CNS of said patient.

Alternatively the medicament stimulating GPE levels may be provided in a mammalian dosage form.

The invention further provides a method of treating patients suffering chronic forms of degeneration of the nervous system by administering GPE and/or analogues thereof over an extended period.

Preferably GPE, and/or analogues thereof (optionally with suitable pharmaceutically acceptable carriers or the like) may be administered to such patients in a form and by a route in which absorbtion takes place across mucous membranes.

Optionally GPE, and/or analogues thereof may be provided as molecules having an electric charge and absorbtion may be aided by an electrophoretic procedure.

Optionally, the invention further provides for the prophylactic use of a substance (GPE or an analogue or a compound that elevates the concentration thereof) to minimise the effects of CNS damage during anticipated events, for example certain procedures such as open-heart surgery)

Although the present invention is defined broadly above, it will be appreciated by those skilled in the art that it is not limited thereto but includes embodiments of which the description provides examples.

BRIEF DESCRIPTION OF DRAWINGS

A better understanding of the invention will be gained from reference to the foregoing examples and drawings wherein.

TECHNICAL DETAILS OF THE INVENTION

Figure 1:
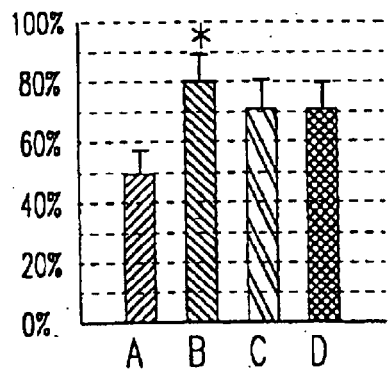
FIG. 1: shows the incidence of cortical infarction following treatment with vehicle alone 50 μg of IGF-1 or the NMDA antagonist MK801 (1 mg) or IGF-1 plus MK801 2 hours after the hypoxia. Similar to previous studies the incidence of cortical infarction was lower in the IGF-1 treated group, whereas MK801 had a lesser effect.

We have explored the observation that insulin-like growth factor 1 (IGF-1) appears to be modified by proteolytic cleavage in nervous tissue to des 1-3N IGF-1, that is IGF-1 missing the 3 amino acids from the amino terminal of the molecule, and to a 3 amino acid peptide gly-pro-glu (GPE) which is the N terminal tripeptide. As des 1-3N IGF-1 also binds to the IGF-1 receptor and GPE does not, the GPE was thought to be of no significance to the neuronal rescue action of IGF-1. Surprisingly, GPE is effective.

Our previous work had shown that the brain increases its production of IGF-1 following brain injury by hypoxia-ischemia and that in addition it increases the synthesis of two specific binding proteins, IGF binding protein-2 (IGFBP-2) and IGF binding protein-3 (IGFBP-3) (Gluckman et al Biochem Biophys Res Commun 182:593–599 1992) and Klemp et al Brain Res 18:55–61 (1992). These were hypothesised to attract the IGF-1 into the region of injury to reach concentrations necessary for neuronal rescue. For this reason IGF-1 was anticipated to be more potent given at a site distant from the injury than des 1-3 N IGF-1 which does not bind well to the binding proteins. This was indeed the case—des 1-3 N IGF-1 was not significantly active as a neuronal rescue agent at a dose equivalent to that at which IGF-1 shows neuronal rescue activity. Thus the prior art pointed to activity at the IGF-1 receptor as the mode of neuronal rescue achieved with IGF-1.

To date, there has been no enabling reference in the prior art to the manipulation of GPE to prevent or treat CNS injury or disease leading to CNS damage in vivo.

Surprisingly we have found that GPE itself appears to be the compound that underlies the phenomenon of neural rescue. (See for instance Example 3). This has led us to propose that treating a patient for neural injury or disease with IGF-1 is a less soundly based proposition, as a tripeptide is easier to prepare, and as it is a more mobile and less immunologically challenging compound therefore it can be expected to be more effective.

Sara (patent EP 0366638 A2) suggested that GPE could act as a neuromodulator to alter the activity of neuronal cells. Because it contains a glutamate and a glycine she suggested that it is likely to act at a NMDA class of receptor either as a partial agonist or antagonist. The classical NMDA receptor antagonist is MK801. We therefore compared the action of IGF-1 to MK801 given after injury and also looked for any additive effect.

Experiment 1 in our specification is a non-limiting example to show that in rats subject to hypoxic-ischemic injury the action of IGF-1 is not mimicked by or added to by use of NMDA receptor antagonist. This study shows that IGF-1 does not act by means of an action to modulate neural activity. In contrast IGF-1, GPE and MK801 all have identical actions on gonadotropin release from hypothalamic tissue (Bourgignon et al Growth Regulation (in press)) suggesting that IGF-1 does act as a probormone for GPE acting to modulate NMDA mediated neuronal activity in terms of hormone release and thus there was no a prior reason to anticipate that GPE would be a neuronal rescue agent. Thus there was no prior art to suggest that IGF-1 might act as a prohormone to form GPE which in turn stops neurones dying. Rather, the prior art suggests that IGF-1 acts via the IGF-1 receptors.

Experiment 2 is a non-limiting example in fetal sheep to show that IGF-1, which induced neuronal rescue in an ischemic model in fetal sheep, did not suppress cortical electroencephalographic activity whereas MK801 does so (Tan et al Ann Neurol 32:677–682 (1992)).

Experiment 3 is a non-limiting example which shows that despite the prior art suggesting that IGF-1 acts as a neural rescue agent via the IGF-1 receptor without modulating neuronal activity, GPE was as potent as a neuronal rescue agent as was IGF-1. The GPE was given shortly after the hypoxic ischemic injury but before degradation of DNA occurs in the regions which are destined in control animals to show neuronal death. The reduced degree of hippocampal neuronal loss and cortical infarction which is a reflection of less neuronal and less glial cell loss due to asphyxia. The mechanism by which GPE leads to prevention of cell death is not known but is clearly not by modulating neuronal activity.

Experiment 4 is a non-limiting example in 21-day old rats to show that GPE has a significant beneficial effect on neuronal outcome when given intraperitoneally, two hours after an insult comprising hypoxia.

Sara has shown GPE to modulate neuronal activity and because agents such as NMDA which do may have some role in treating neuronal injury suggested but did not provide any evidence for its use as a treatment for neurological disease. However there is no prior art for our claims which are that GPE can be used to prevent neurological disease by preventing neurones and glia from dying. The type of clinical application to which our invention is directed is totally different from that of Sara.

More recent work by us tends to support the finding that the effects of GPE are most developed in the hippocampus itself; the CA1-2 regions. Thus our data relating to GPE and the like may be in the first instance most relevant to diseases primarily involving the hippocampus, and in the second instance to other populations of neurones once the modus operandi is better understood.

Description of the Preferred Embodiments

The invention relates to a method of manipulating neural damage. In a first aspect, the invention relates to a method of treating CNS damage after an injury to the CNS occurs. For example, the patient may have suffered perinatal asphyxia or asphyxia or cerebral ischemia associated with a stroke or other non-limiting examples of CNS injuries having been described earlier herein. In these instances, it is desirable to reduce or eliminate the symptoms of CNS damage.

CNS damage may for example be measured clinically by the degree of permanent neurological deficit cognitive function, and/or propensity to seizure disorders. (In our experiments we have used histological techniques).

It is proposed that the concentration of GPE and/or analogues thereof in the CNS and in the brain of the patient in particular should be increased in order to treat the CNS damage. Accordingly, GPE and/or analogues thereof can be administered directly to the patient. By the term "GPE" we refer in particular to gly pro glu or gly pro or pro glu. By analogues of GPE is meant compounds which exert a similar biological effect to GPE. These compounds can be derived from humans or other animals. GPE and analogues can be purified from natural sources or produced by synthetic techniques. Synthetic GPE can be obtained commercially.

Alternatively, compounds can be administered which, upon administration to the patient, increase the active concentration of GPE and/or naturally occurring analogues thereof in the CNS. By "active concentration" is meant the biological concentration of GPE and/or analogues in the CNS of the patient able to exert an effect on CNS damage. For example, elevating the active concentration of IGF-1 may enhance the formation of GPE.

GPE, analogues thereof and compounds which elevate the active concentrations thereof can be administered centrally or systemically. Desirably, the compositions are administered directly to the CNS of the patient. Accordingly, the compositions may be administered directly into the brain or cerebrospinal fluid by techniques including lateral ventricular through a burrhole, or anterior fontanelle, lumbar or cisternal puncture or the like.

If desired, a combination of the compounds can be administered. In addition they may be re-administered with other agents or growth factors, for example, transforming growth factor beta (TGF-β).

The foregoing experiments show that the expression of IGF-1 after a neural insult follows a specified time course and occurs in specified areas of the body. Accordingly, the compositions should be administered according to the pattern of CNS injury and the elapsed time subsequent to an injury so as to produce the most desirable results. The compositions may be administered directly to the region of the body where the greatest CNS injury has occurred.

The compositions may for example be administered about 0.5 to 100 hours after an injury and only one treatment may be necessary. Alternatively, repeated treatment may be given to the patient.

A suitable dosage range may for example be between about
0.1 to 1000 µg of GPE (and/or analogues or compounds that elevate the concentrations thereof) per 100 gm of body weight where the composition is administered centrally.

The treatment may be given before (as well as after) an injury—as for example before elective surgery. Examples of relevant elective procedures include neural surgery, in which retraction of lobes of the brain may lead to cerebral oedema, or heart operations, such as valve replacement, in which inevitable small emboli are said to lead to detectable impairment of brain function in some 75% of cases.

The invention also relates to a medicament for treating CNS injury. The medicament can comprise GPE and/or analogues thereof or a compound which elevates the concentration of GPE in the CNS such as IGF-1. The compounds are desirably provided in a pharmaceutically acceptable carrier or diluent such as those known in the art. GPE, analogues and compounds that elevate the concentration thereof can be manufactured by peptide synthesis techniques. Alternatively, the compounds can be isolated from natural sources.

A compound with little or no immunological effect may be administered over long periods, as long as other side effects prove to be unimportant. We propose that oral doses of a pharmaceutical compound promoting higher GPE levels in the brain (such as GPE itself) may be given over long periods to (for example) sufferers from chronic CNS disturbances such as Parkinson's disease, multiple sclerosis, Alzheimer's disease, and the like. In this instance the tripeptide nature of GPE should allow its entry into the circulation by direct absorbtion from the buccal mucosa from a lozenge placed under the tongue. We have shown that GPE is effective by intraperitoneal administration (in young rats) so it is at least not limited to injection into the CSF The efficacy of GPE therapy in such diseases may be difficult to establish unless clinical trials are attempted.

The invention is supported by the following experimental data. In the following studies it was found that:
1) The neuronal rescue effect of IGF-1 is not mimicked or added to by use of an NMDA receptor antagonist.
2) Unlike an NMDA receptor antagonist neuronal rescue therapy with IGF-1 does not suppress seizure activity. Thus, the neuronal rescue effects of treatment with IGF-1 are not primarily mediated via the NMDA receptor.
3) Alterations in CNS levels of the n terminal tripeptide of IGF-1 called GPE can alter CNS damage resulting as a consequence of an injury to the CNS.

The present invention is further illustrated by the following examples. These examples are offered by way of illustration only and are not intended to limit the invention in any manner. All patent and literature references cited throughout the specification are expressly incorporated. The studies described were approved by the Animal Ethical Committee of the University of Auckland.

EXPERIMENT 1

The objective of this study was to compare the effects of administering IGF-1 and the NMDA receptor antagonist MK801 after a CNS injury in order to clarify the site of action of IGF-1. The experiments involved treating the rats with vehicle, IGF-1, MK801 or IGF-1 plus MK801 2 hours after a CNS injury. These rats had an hypoxic-ischemic injury to one cerebral hemisphere induced in a standard manner. One carotid artery was ligated and the animal was subjected two hours later to a defined period of inhalational hypoxia. The degree, length of hypoxia, ambient temperature and humidity were defined to standardise the degree of damage. They were sacrificed five days later for histological analysis using stains (acid-fuchsin) specific for necrotic neurons. In such experiments cell death typically is restricted to the side of the side of arterial ligation and is primarily in the hippocampus, dentate gyrus and lateral cortex of the ligated hemisphere.

Adult Wistar rats (68 280–320 g) were prepared under 3% halothane/$O_2$ anaesthesia. The right side carotid artery was ligated. A guide cannula was placed on the dura 8.2 mm anterior from bregma and 1.4 mm from midline on the right. The rats were allowed to recover from anaesthesia for 1 hour and were then placed in an incubator with humidity 85±5% and temperature 34±0.5C. for 1 hour before hypoxia. Oxygen concentration was reduced and maintained at 6±0.2 $O_2$% hypoxia for 10 minutes. The rats were kept in the incubator for two hours after the hypoxia then treated either with IGF-1 (n=17), MK801 (n=17), MK801 plus IGF-1 (n=17) or vehicle (n=17) alone. Fifty micrograms of IGF-1 or vehicle alone (0.1% BSA in 0.15M PBS (pH 7.3)) were given via intra-ventricular (IVC) infusion. Simultaneously the rats were treated subcutaneously (IP) using 1 mg MK801/0.5 ml or saline alone. The intraventricular injections of 50 $\mu$g IGF-1 or vehicle alone were made into the right lateral ventricle at 1 $\mu$l/minute under 1.5%–2% halothane anaesthetic. Rats in each treatment group were infused simultaneously. The rats had free access to food during experiment and were euthanized at 120 hours after hypoxia with overdose of sodium pentobarbitol. Briefly, the brain was perfused in-situ with FAM (Formaldehyde, Acetic Acid, Methanol 1:1:8) then paraffin embedded. The sections were stained with Thionin and Acid Fuchsin. The presence of cortical infarction, defined as a region of tissue death or parenchymal pan-necrosis due to death of glia as well as neurons, was determined via light microscopy by an assessor who was blinded to the experimental groupings.

Results are illustrated in FIG. 1, showing the ratio between the R (ligated carotid) and L sides of the brains, wherein column A is vehicle, column B is 50 $\mu$g IGF-1, column C is 1 mg MK801, and column D is 50 $\mu$g IGF-1 with 1 mg MK801. (p(*)=0.031).

Similar to previous studies by ourselves the incidence of cortical infarction was lower following IGF-1 treatment (33%) compared to 65% in controls (Guan et al J Cereb Blood Flow metab 13: 609–616 (1993)); whereas following MK801 treatment the incidence was 50%. The combination of IGF-1 and MK801 was 41%. Thus in rats subject to hypoxic-ischemic injury the action of IGF-1 is not mimicked by or added to by use of NMDA receptor antagonist

EXPERIMENT 2

The objective of this study was to compare the effects of treatment either with IGF-1 (see FIG. 2) and previously published work with the NMDA antagonist MK810 after an ischemic brain injury on postischernic seizures and neuronal losses in fetal sheep. (Tan et al Ann Neurol 32:677–682 (1992)).

The methods were those of an earlier study (Tan et al Ann Neurol 32:677–682 (1992)). Briefly, late gestation fetal sheep were chronically instrumented to record EEG, nuchal activity and blood pressure, and were then returned to the uterus. Cortical EEG activity, nuchal activity and blood pressure were recorded throughout he experiment and the fetal brain subjected to 30 minutes of ischemia. Two hours later they were treated by an infusion of either 1 $\mu$g IGF-1 (n=6) or vehicle (artificial CSF) (n=6) into the lateral ventricle. Five days later the brains were fixed and assessed for neuronal loss as described previously (Tan et al Ann Neurol 32:677–682 (1992)).

Figure 2:
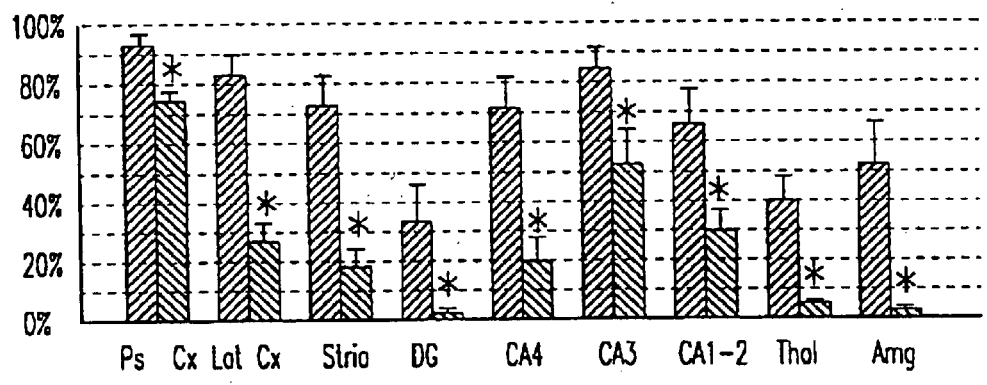
FIG. 2: shows an example of the effects of treatment with 1 μg IGF-1 2 h after an ischemia in fetal sheep. The names under the horizontal axis are standard abbreviations for various portions of the brain. This dose was neuroprotective but, unlike MK801, did not suppress seizures.

FIG. 2 shows the neuronal loss scores for a number of regions of the brain (identified by abbreviations on the horizontal axis) as a percentage of the untreated side. In all cases the vehicle is the left-hand column and the effects of 1 $\mu$g of IGF-1 is on the right.

The results show that, unlike the NMDA antagonist treated sheep, where electrical activity was markedly suppressed (Tan et al Ann Neurol 32:677–682 (1992)), IGF-1 rescued neurons (FIG. 2) but did not suppress the postischemic seizure activity in fetal sheep. This study also suggests that the neuroprotective effects of IGF-1 does not primarily occur via the NMDA receptor or altered electrical activity of the brain.

EXPERIMENT 3

The objective of this study was to compare the effects of treatment with GPE to that of vehicle given 2 hours after a hypoxic-ischemic brain injury.

The dose of 3 $\mu$g of GPE was chosen to be equivalent to that present in 50 $\mu$g of IGF-1 which has previously been shown to be neuroprotective (Guan et al J Cereb Blood Flow Metab. 13:609–616 (1993)). Unilateral hypoxic-ischemic injury was induced in adult 300±10 g) male Wistar rats. The rats underwent unilateral carotid ligation under light halothane anaesthesia. Following one hour recovery they were placed in an incubator at 34 C. at 85±5% humidity for one hour before injury. They were subjected to 10 min inhalational asphyxia (FiO2 6.0%) and maintained in the incubator for one hour after asphyxia. Two hours after the termination of the inhalational injury, a single stereotaxically controlled lateral cerebroventricular injection of either 3 $\mu$g GPE (n=15) or phosphate buffered saline alone (n=15) was given. The animals were then maintained for 120 hrs, anaesthetized and the brains fixed in situ for histological assessment.

Figure 3:
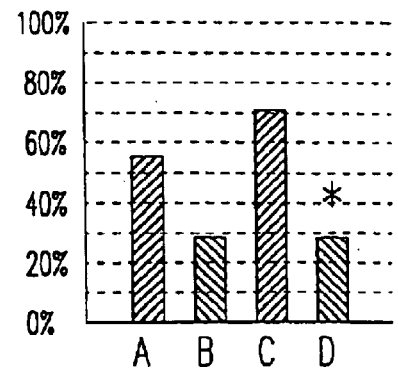
FIG. 3: shows the incidence of cortical infarction and hippocampal damage following treatment with 3 μg GPE or vehicle 2 hours after the hypoxia. [The incidence of hippocampal damage was reduced following treatment with 3 μg GPE. * $p<0.05$]

Surviving and dead neurons were discriminated with the use of a thionin/acid fuchsin staining technique [C. Williams, A. Gunn, C. Mallard, P. Gluckman Ped Res, (1990). A. Brown, J. Brierley, J. Neurol Sci, 16: 59–84 (1971)]. The results are shown in FIG. 3; using a scoring technique. It is evident that there was neuronal damage even on the unligated side, yet GPE therapy reduced the incidence of hippocampal damage in the ligated hemisphere compared to the vehicle treated controls (p<0.05 by Fisher's exact test). Similar to our previous study with IGF-1 the incidence of cortical infarction was lower following GPE treatment at 27% compared to the control/vehicle treated rats at 53% (Guan et al J Cereb Blood Flow Metab. 13:609–616 (1993)).

FIG. 3 shows the incidence of cortical infarction (columns A and B) and hippocampal damage (columns C and D) following treatment with vehicle (columns A and C) or 3 $\mu$g GPE (columns B and D) two hours after the hypoxia. [The incidence of hippocampal damage was reduced following treatment with 3 $\mu$g GPE. The asterisk indicates a probability p of under <0.05.

Figure 4:
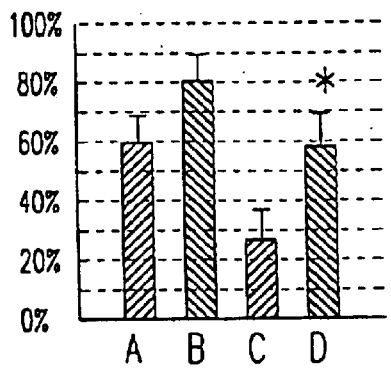
FIG. 4: shows results from the same experiment; wherein the two columns on the left shown the area (hence volume, from stereology) of viable cortical tissue remaining after treatment, as a ratio between the right side of the brain and the left (injured) side, while the two columns labelled CA-1 show the proportion of live neurones remaining (comparing right and left sides) after the insult.

FIG. 4 shows a later, more critical assessment of the same experiment. For this figure the columns A and B indicate the proportional loss of area (which can be extrapolated to indicate volume using the well-known principles of stereology) between the left and right sides of the cortex of the brain, for either a control vehicle or 3 $\mu$G of GPE. Volumes were measured using computer-aided image analysis techniques. Columns C and D relate to the hippocampus and indicate the proportion of live neurones remaining after the experiment; again comparing right and left side counts. The asterisk indicates a probability of 0.04. Neurones were counted after staining, with the aid of a microscope. The administration of GPE has resulted in a significant reduction in the number of damaged cells. Thus a single central injection of GPE following an asphyxial injury in the adult rat was associated with a marked improvement in outcome as assessed histologically.

A histological experiment to locate GPE binding sites within the rat brain employed quantitative receptor autoradiography to locate [3H]-GPE binding in coronal sections of the brain as previously described in Dragunow et al (1988, Brain Research 462, 252–257). Fresh frozen brain sections were cut on a cryostat and stored at −80 deg C until use. Sections were then thawed and pre-incubated with 50 mM Tris HCI (pH 7.4) for 10 minutes at room temperature (250 $\mu$l per section). Sections were then dried and 250 $\mu$l per section of $5 \times 10^5$ counts/min$^{-1}$ of [3H]-GPE also made up in Tris HC1 buffer (50 mM, pH 7.4) was added for 1 hour at room temperature. Sections were then washed two times for one minute each in ice-cold Tris-HCI followed by one rinse for 1 minute in ice-cold distilled water. Sections were then dried overnight at 4 deg C. and apposed to [3H] sensitive film for 2 weeks, and then developed to produce autoradiograms.

Figure 6:
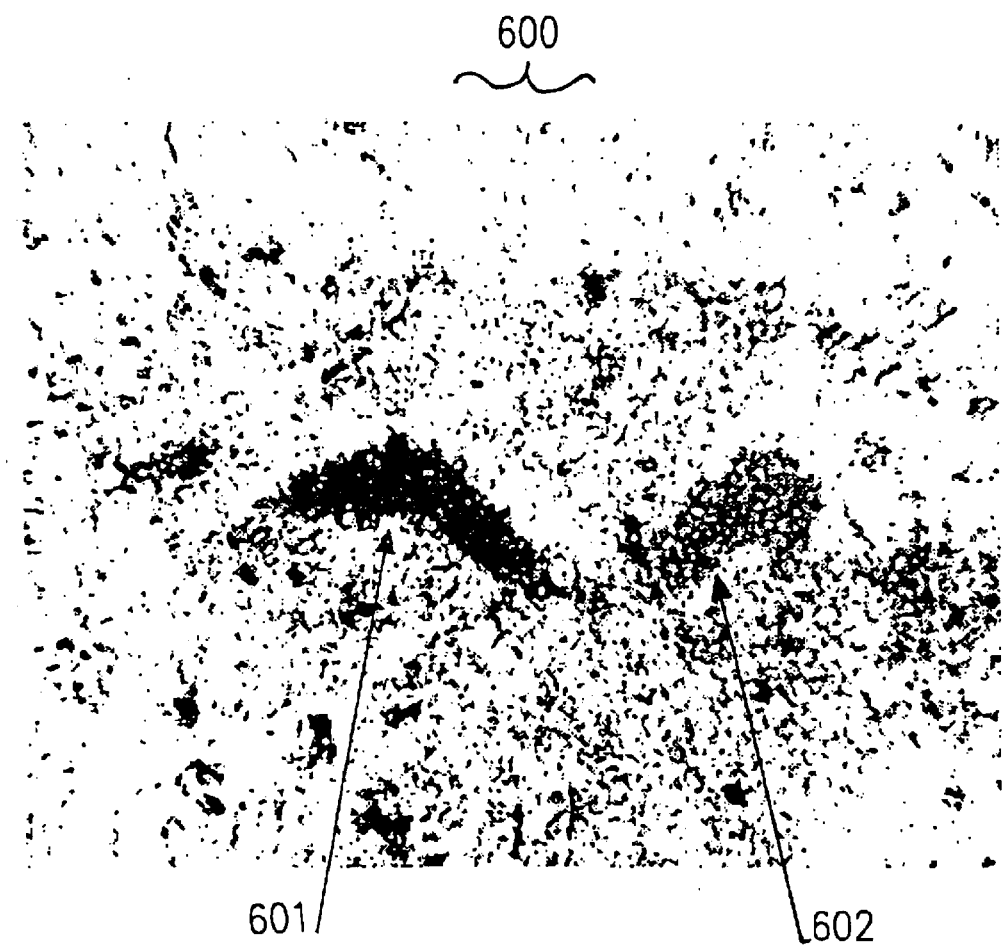
FIG. 6: is a photomicrograph which shows binding of GPE in an injured side of the hippocampus.

Results as illustrated in FIG. 6 show that the left hippocampus has bound the radioactive material while the corresponding side on the right shows little reaction. The neurons on this side were absent due to a pre-existing injury. This radioautograph illustrates a particular binding site for GPE and tends to support our belief that GPE provides particular benefit at this important nucleus.

SUMMARY OF EXPERIMENTS

GPE (in these experiments, dissolved in 0.15M phosphate buffered saline) administered in a single dose given in the period commencing with the time of the CNS injury through to about 8 hours thereafter (and including a time point of about 2 hours after the neural injury has shown therapeutic effect in reducing or eliminating the severity of CNS damage suffered after a neural injury. GPE is especially useful in reducing neuronal loss, infarction, and loss of glial and other cells associated with CNS injury. Thus it can be seen that in at least the preferred forms of the invention a method and/or medicament for treating CNS damage is provided which is able to substantially prevent or treat CNS damage. CNS damage may be associated with asphyxia, hypoxia, toxins, infarction, ischemia or trauma. It will be appreciated that the main application of the invention is to humans. However, the usefulness of the invention is not limited thereto and treatment of other non-human animals, especially mammals is also within the scope of the invention.

The present invention, therefore, recognises the role of an administration of a medicament comprising GPE and/or other compounds of similar effect into a patient at or following a CNS injury with the consequential result that CNS damage is minimised by preventing the otherwise consequential, self-induced damage that would occur following the injury, i.e. it is not involved with the repair of damage that has already occurred but to a treatment at, or subsequent, to the injury but before the consequential long term damage occurs thereby minimising the occurrence of such damage.

EXAMPLE 1

Alleviation of Brain Damage to an Infant or Neonatal Mammal Resulting from Perinatal Asphyxia.

Basing the dose rates on our rat and fetal sheep models a suitable method for alleviation of brain damage is to infuse the infant's circulation by intravenous rout with GPE or an analogue thereof in normal saline at a preferred dose rate in the range 0.1 $\mu$g/kg to 10 mg/kg and more preferably about 1 mg/kg from within about 12 h of the onset of fetal distress until about 120 h later. A higher loading dose may be used at the commencement of treatment. Alternatively GPE may initially be administered via the maternal circulation in a higher intravenous dose rate of about 5 mg/kg, while the placenta is largely functional. Alternatively intraventricular infusion at about 10 kg/kg in artificial CSF into the lateral ventricle may be used in indicated.

EXAMPLE 2

Alleviation of Brain Damage to Human or Mammal Resulting from Stroke.

Basing the dose rates on our rat and fetal sheep models a suitable method for alleviation of brain damage is to infuse the patients circulation by intravenous route with GPE or an analogue thereof in normal saline at a preferred dose rate in the range of 0.1 $\mu$g/kg to 10 mg/kg and more preferably about 1 mg/kg from within about 12 h of the onset of neurological signs until about 120 h later. A higher loading dose may be used at the commencement of treatment. Alternatively the same dose may be administered by close carotid injection. Alternatively intraventricular infusion at about 10 $\mu$g/kg in artificial CSF into the lateral ventricle may be used if indicated.

EXAMPLE 3

Alleviation of Brain Damage to Human and Mammal Resulting from Intracerebral Haemorrhage.

Basing the dose rates on our rat and fetal sheep models a suitable method for alleviation of brain damage is to infuse the patients circulation intravenous route with GPE or an analogue thereof in normal saline at a preferred dose rate in the range of 0.1 $\mu$g/kg to 10 mg/kg and more preferably about 1 mg/kg until about 120 h after the onset on the haemorrhage. A higher loading does may be used at the commencement of treatment. Alternatively intraventricular infusion at about 10 $\mu$g/kg in artificial CSF into the lateral ventricle may be used if indicated.

EXAMPLE 4

Alleviation of Brain Damage to Human or Mammal Resulting from Traumatic Head Injury.

Basing the dose rates on our rat and fetal sheep models a suitable method for alleviation of brain damage is to infuse the infant's circulation by intravenous route with GPE or an analogue thereof in normal saline at a preferred does rate in the range of 0.1$\mu$g/kg to 10 mg/kg and more preferably about 1 mg/kg from within about 12 h of the injury until about 120 h later. A higher loading dose may be used at the commencement of treatment. Alternatively intraventricular infusion at about 10 $\mu$g/kg in artificial CSF into the lateral ventricle may be used if indicated.

EXAMPLE 5

Peripheral Administration of GPE is Effective.

The objective of this study was to compare the effects of treatment with GPE to that of a vehicle given 2 hours after an hypoxic-ischemic injury. The dose range of 2 to 200 $\mu$g was chosen to span a range of systemic doses that are greater than that required centrally (see experiment 3).

Unilateral hypoxic-ischemic injury was induced in 21 day old, 45±5 g Wistar rats. The rats underwent unilateral carotid ligation under light halothane anaesthesia.

Following one hour recovery they were placed in an incubator at 34 deg C. 85±5% humidity for one hour before the injury. They were subjected to 1 min inhalation hypoxia (FiO2 8.0%) and then returned to room temperature (22 deg C.) and normoxia. Two hours after the termination of the injury, a single intraperitoneal injection of 0.25 ml of 2, 20 or 200 μg GPE per rat, or saline alone was given. The animals were then maintained for 120 hrs, anaesthetized and the brains were fixed for histological assessment.

Figure 5:
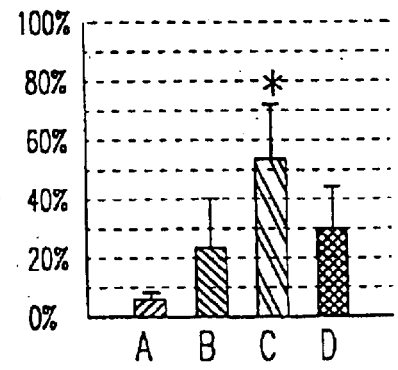
FIG. 5: shows the dose-response effect of GPE on neuronal outcome in the hippocampus (CA1-2 region), after peripheral (intraperitoneal) administration of GPE. The vertical axis shows the R/L ratio; the ratio between the unligated and the ligated sides of the brain.

Surviving and dead neurons were discriminated using the thionin/acid fuchsin staining technique (Guan et al J Cereb Blood Flow Metab. 13:609–616 (1993). The results, in which the height of a point is given by the ratio as a percentage of live neurones in the CA1-2 region on the right side to the number on the left side are shown in FIG. 5. Column A is vehicle, column B is 2 μg of GPE, column C is 20 μg of GPE, and column D is 200 μg of GPE. In this figure, the P value (0.031) was calculated by a method using one way ANOVA comparing many groups after Arcsin transformation.

GPE therapy (20 μg) reduced the loss of neurons in the CA1-2 region of the hippocampus (p<0.05). Thus a single peripheral injection of GPE following an asphyxial injury in the rat was associated with a marked improvement in outcome as assessed histologically.

Options: Our choice of the intraperitoneal route was at least partly dictated by the difficulty of any other routes in such small animals. While it is likely that the intraperitoneal route offers better access of GPE to the circulation and hence to the blood-brain barrier, other routes such as intravenous, intramuscular, or subcutaneous routes also appear to be available although the effective dose rate is likely to be greater.

The above experiment shows that the advantages of GPE over previously favoured IGF-1 treatments include that it (unlike IGF-1) can cross the blood-brain barrier and so can gain access to the CNS from a peripheral site.

Pharmacology

Apart from the dose-response experiments on which FIG. 5 is based, we have not yet studied the pharmacological properties of GPE. We expect it to have a similar half-life in blood to other peptides; we expect that the liver and kidneys will relatively rapidly take up circulating GPE, and we expect that it has a relatively large therapeutic ratio. In view of the expected rapid uptake, intravenous administration is preferably in the form of a steady infusion.

Advantages

Some advantages offered by this invention, especially over IGF-1 and the like include:

(1) The active ingredients are easy to synthesise either in vitro or by other means such as by recombinant techniques.
(2) The small molecule can diffuse readily through the body and between compartments (e.g. the blood-brain barrier, and mucous membranes), aiding in the choice of methods for its administration and its ability to reach sites where injury has occurred.
We have shown that intraperitoneal administration, to give one non-CSF example, is effective.
(3) The small molecule is unlikely to present a challenge to the immune system, so it may be administered over extended periods and it may be administered prophylactically.
(4)) Species differences are unlikely to be important.

Although the present invention is defined broadly above, it will be appreciated by those skilled in the art that it is not limited thereto but includes embodiments of which the description provides examples. Finally, it will be appreciated that various alterations and modifications may be made to the foregoing without departing from the scope of this invention as claimed.

What is claimed is:

1. A method for protecting glial cells or non-dopaminergic neural cells in a mammal against death from neural injury or disease comprising the step of administering to said mammal a neuroprotective amount of a peptide selected from the group consisting of (a) the tripeptide gly-pro-glu (GPE); (b) the dipeptide gly-pro (GP); and (c) the dipeptide pro-glu, wherein said peptide decreases cell death or degeneration.

2. A method as claimed in claim 1 wherein the peptide administered GPE.

3. A method as claimed in claim 2 wherein the GPE is administered to protect non-dopaminergic neurons against death.

4. A method as claimed in claim 2 wherein GPE is administered to protect glial cells against death.

5. A method as claimed in claim 3 wherein the dosage range of GPE administered is from about 1 μg to about 1000 mg of GPE per kg of body weight of the mammal.

6. A method as claimed in claim 4 wherein the dosage range of GPE administered is from about 1 μg to about 1000 mg of GPE per kg of body weight of the mammal.

7. A method as claimed in claim 2, further comprising applying an electrophoretic procedure in aid of said administration of GPE.

8. The method of claim 1, wherein said peptide is administered via maternal circulation.

9. A method as claimed in claim 2 in which a neuroprotective amount of GPE is administered prior to an event considered likely to lead to an injury to glial cells or non-dopaminergic neural cells.

10. The method of claim 9, wherein said event comprises cardiac surgery.

11. The method of claim 9, wherein said event comprises brain surgery.

12. The method of claim 9, wherein said event comprises parturition.

13. The method of claim 2, wherein said peptide is administered via maternal circulation.

14. A method as claimed in claim 9, wherein said event is considered likely to lead to an injury to glial cells.

15. A method as claimed in claim 2 in which GPE is administered subsequent to injury or disease affecting glial cells or non-dopaminergic neural cells but prior to death of said cells.

16. A method as claimed in claim 15, wherein said injury or disease affects non-dopaminergic neural cells.

17. A method as claimed in claim 15, wherein said injury or disease affects glial cells.

18. A method as claimed in claim 15, wherein said GPE is administered to protect glial non-dopaminergic neural cells against death through injury, and wherein said GPE is administered for up to 100 hours subsequent to said injury.

19. A method as claimed in claim 18 in which GPE is administered from 0.5 to to 8 hours subsequent to said injury.

20. A method as claimed in claim 2 in which GPE is administered directly to where the cell bodies of glial cells or non-dopaminergic neural cells to be protected are located.

21. A method of claim 20, wherein said cells to be protected comprise glial cells.

22. A method as claimed in claim 20 wherein GPE is administered directly to the brain or cerebrospinal fluid by cerebro-ventricular injection, by injection into the cerebral parenchyma or through a surgically inserted shunt into the lateral cerebral ventricle of the brain.

23. A method as claimed in claim 20 wherein GPE is administered by cerebro-ventricular injection.

24. A method as claimed in claim 2 wherein GPE is administered in combination with artificial cerebrospinal fluid.

25. A method as claimed in claim 23 wherein GPE is administered in combination with artificial cerebrospinal fluid.

26. A method as claimed in claim 2, wherein GPE is administered through an intravenous, oral, rectal, nasal, subcutaneous, inhalation, intraperitoneal or intramuscular route.

27. A method as claimed in claim 26 wherein GPE is administered by intraperitoneal injection.

28. The method of claim 1 wherein said neural injury is hypoxic neural injury.

29. The method of claim 1 wherein said neural injury is ischemic neural injury.

30. The method of claim 28 wherein said hypoxic injury results from stroke or cardiac bypass surgery.

31. The method of claim 29 wherein said ischemic injury results from stroke or cardiac bypass surgery.

32. A method of treating injury in a mammal comprising administering an effective amount of a peptide selected from the group consisting of gly-pro-glu, gly-pro, and pro-glu.

33. The method of claim 5, wherein said neural injury is selected form the group consisting of hypoxic neural injury, ischemic neural injury and traumatic injury.

34. The method of claim 6, wherein said hypoxic neural injury or said ischemic neural injury is associated with one or more of stroke and cardiac bypass surgery.

35. The method of claim 1, wherein said glial cells or non-dopaminergic neural cells are central nervous system cells.

36. The method of claim 1, wherein said glial cells or non-dopaminergic neural cells are peripheral nervous system cells.

37. A method for protecting glial cells in a mammal against death from neural injury or disease comprising the step of administering to said mammal a protective amount of a peptide selected from the group consisting of (a) the tripeptide gly-pro-glu (GPE); (b) the dipeptide gly-pro (GP); and (c) the dipeptide pro-glu, wherein said peptide decreases cell death or degeneration of glial cells.

* * * * *

UNITED STATES PATENT AND TRADEMARK OFFICE
CERTIFICATE OF CORRECTION

PATENT NO. : 6,780,848 B2
DATED : August 24, 2004
INVENTOR(S) : Gluckman et al.

It is certified that error appears in the above-identified patent and that said Letters Patent is hereby corrected as shown below:

<u>Title page,</u>
Item [*] Notice, should read:
-- Subject to any disclaimer, the term of this patent is extended or adjusted under 35 U.S.C. 154(b) by 128 days. --.

Signed and Sealed this

Eighth Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,780,848 B2  Page 1 of 1
APPLICATION NO. : 09/910461
DATED : August 24, 2004
INVENTOR(S) : Gluckman et al.

It is certified that error appears in the above-identified patent and that said Letters Patent is hereby corrected as shown below:

Column 14,
Line 10, between "administered" and "GPE" insert -- is --.

Column 14,
Line 11, delete "the".

Column 14,
Line 50, between "glial" and "non-dopaminergic" insert -- or --.

Column 16,
Line 2, delete "form" and insert therefore -- from --.

Signed and Sealed this

Twenty-sixth Day of December, 2006

JON W. DUDAS
*Director of the United States Patent and Trademark Office*